(12) United States Patent
Schulte et al.

(10) Patent No.: US 9,162,053 B2
(45) Date of Patent: Oct. 20, 2015

(54) DIRECTIONAL LEAD ASSEMBLY

(75) Inventors: Gregory T. Schulte, Minneapolis, MN (US); Scott Kokones, Boston, MA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 776 days.

(21) Appl. No.: 13/076,874

(22) Filed: Mar. 31, 2011

(65) Prior Publication Data

US 2011/0245903 A1     Oct. 6, 2011

Related U.S. Application Data

(60) Provisional application No. 61/320,539, filed on Apr. 2, 2010, provisional application No. 61/320,584, filed on Apr. 2, 2010.

(51) Int. Cl.
*A61N 1/05* (2006.01)
*A61N 1/04* (2006.01)
*A61N 1/375* (2006.01)

(52) U.S. Cl.
CPC ............ *A61N 1/0534* (2013.01); *A61N 1/0551* (2013.01); *A61N 1/05* (2013.01); *A61N 1/375* (2013.01); *Y10T 29/49172* (2015.01)

(58) Field of Classification Search
CPC . A61N 1/0529; A61N 1/0534; A61N 1/0551; A61N 1/05
USPC ............... 607/115–117, 45; 600/372–373, 600/377–378, 393; 29/874, 876
See application file for complete search history.

(56) References Cited

U.S. PATENT DOCUMENTS

| | | | |
|---|---|---|---|
| 5,713,922 A | 2/1998 | King | |
| 6,018,684 A | 1/2000 | Bartig et al. | |
| 6,510,347 B2 | 1/2003 | Borkan | |
| 7,668,601 B2 | 2/2010 | Hegland et al. | |
| 8,046,909 B2 * | 11/2011 | Dye et al. | 29/825 |
| 2003/0236562 A1 | 12/2003 | Kuzma | |
| 2006/0168805 A1 * | 8/2006 | Hegland et al. | 29/854 |
| 2006/0259106 A1 | 11/2006 | Arnholt et al. | |
| 2008/0114230 A1 | 5/2008 | Addis | |
| 2008/0255647 A1 * | 10/2008 | Jensen et al. | 607/119 |
| 2008/0269854 A1 | 10/2008 | Hegland et al. | |
| 2009/0204193 A1 | 8/2009 | Kokones et al. | |
| 2010/0268298 A1 * | 10/2010 | Moffitt et al. | 607/45 |
| 2011/0130816 A1 * | 6/2011 | Howard et al. | 607/116 |

OTHER PUBLICATIONS

European Patent Office, Supplemental European Search Report in European patent application No. 11763416.2, dated Aug. 28, 2013, 6 pages.
United States Patent and Trademark Office, the International Search Report and Written Opinion in International application No. PCT/US2011/030676, mailed Jun. 1, 2011.

* cited by examiner

*Primary Examiner* — Carl H Layno
*Assistant Examiner* — Jon Eric C Morales
(74) *Attorney, Agent, or Firm* — Lowe Graham Jones PLLC; Bruce E. Black

(57) ABSTRACT

Leads having directional electrodes thereon. Also provided are leads having directional electrodes as well as retention ledges to secure the electrodes to the leads. Also provided are leads with directional electrodes where all the electrodes have the same surface area. Methods of manufacturing leads and methods of treating conditions and selectively stimulating regions of the nervous system are also provided.

19 Claims, 19 Drawing Sheets

DIRECTIONAL LEAD ASSEMBLY

CROSS-REFERENCE

This application claims priority to U.S. Provisional Application Ser. Nos. 61/320,539 and 61/320,584, both filed Apr. 2, 2010.

FIELD OF INVENTION

The present invention relates to implantable or otherwise insertable electrical leads having directional electrodes thereon.

BACKGROUND

Neuromodulation, such as deep brain stimulation, spinal cord stimulation, and nerve stimulation, is becoming an increasingly preferred form of therapy for certain neurological conditions and disorders when other forms of therapy are not effective. An implantable neurological stimulation system may be used to treat conditions such as pain, movement disorders, epilepsy, depression and other medical conditions. A neurostimulation system typically includes a pulse generator and an electrical stimulation lead. A lead extension may also be used. Electrical stimulation leads have one or more electrodes, which may be positioned within or proximate to a specific location in a patient to deliver electrical energy to a target location in the patient. Some therapies involve electrical stimulation of the brain or spinal cord. Still other therapies involve electrical stimulation of other sites in the patient.

As one example, deep brain stimulation (DBS) involves delivery of electrical stimulation to nerve structures in specific areas of the brain to either excite or inhibit cell activity. A stimulation lead is typically implanted at a desired location within the brain with relative precision using magnetic resonance (MR) imaging techniques (or other imaging techniques) and stereotactic guidance. DBS can be effective in the management of, for example, chronic pain, movement disorders such as Parkinson's disease and essential tremor, epilepsy, and psychiatric disorders such as depression and obsessive-compulsive disorder.

Precise placement of the stimulation lead within the brain or other neural structure, such as the spinal cord or a nerve is important. In some applications, it is desirable to position the stimulation lead to deliver stimulation to a very small target site without stimulating adjacent neural tissue. If stimulation is not delivered with precision to a desired target site, adjoining areas may also be stimulated, which may lead to undesirable side effects.

U.S. Pat. No. 7,668,601 to Hegland et al. describes a medical lead having at least one segmented row of electrodes as well as at least one ring electrode. A preferred embodiment includes two ring electrodes and two rows of segmented electrodes, with each row of segmented electrodes including three or four electrodes each. The ring electrode is defined as extending substantially around the entire periphery of the lead body, and the segmented electrodes are defined as extending around only a portion of the entire periphery. Hegland emphasizes that the ring electrode may act as a fall-back for stimulation if the rows of segmented electrodes are not positioned proximate to the physiologically appropriate tissue for stimulation (col 3, lines 27-30).

U.S. Pat. No. 6,510,347 to Borkan describes a stimulation catheter having in-line directional electrodes. The directional electrodes are described as extending 30 to 270 degrees around the circumference of the sheath. Borkan describes that a directional electrode is preferred for spinal cord stimulation to provide a more localized stimulation region and reduce power requirements of the neuromodulation system. In a preferred embodiment Borkan describes three in-line electrodes, each extending 270 degrees.

Current electrical leads used in neuromodulation, do not provide a uniform longitudinal distribution of charge while also allowing for directional stimulation with large electrode surface area. A non-uniform longitudinal distribution of charge can make it difficult to predict the electrical field generated by selected electrodes. Further, although band electrodes are unlikely to become unintentionally detached from the periphery of the lead body since they encircle the lead body, directional electrodes do not extend around the entire periphery of the lead. Therefore directional electrodes, also known as partial or segmented electrodes, can possibly detach from the lead body, especially when being passed through a guide cannula during the implant procedure. However, an electrode with retention features that extend inward to the lead axis may require the lead diameter to be increased in order to accommodate features internal to the lead body, such as electrical conductors and/or a stylet lumen.

SUMMARY

In an embodiment, the present invention provides an electrical lead comprising a cylindrical lead body having at least one directional electrode, as defined in more detail below, and at least one unitary electrode, as defined in more detail below, disposed on a distal end thereof. In a preferred embodiment, the at least one directional electrode is a plurality of directional electrodes and the at least one unitary electrode is a plurality of unitary electrodes. In certain embodiments, the plurality of directional electrodes are arranged as rows of directional electrodes along the longitudinal axis of the lead. In certain embodiments, the unitary electrode(s) has exposed portions that are aligned longitudinally with the directional electrodes. In a preferred embodiment, the lead comprises two unitary electrodes with three exposed portions aligned longitudinally with two rows of three directional electrodes. The unitary electrodes and rows of directional electrodes can be arranged in any order. For example, the two rows of three directional electrodes each can be located between the two unitary electrodes (referred to herein as a "1-3-3-1" configuration); the two unitary electrodes can be located between the two rows of three directional electrodes each (referred to herein as a "3-1-1-3" configuration), or the unitary electrodes and the rows of three directional electrodes can alternate (referred to herein as a "1-3-1-3" configuration or a "3-1-3-1" configuration).

In another embodiment, the present invention provides a lead comprising a cylindrical lead body having a plurality of directional electrodes on a distal end thereof. Preferably the directional electrodes are arranged in three rows along the longitudinal axis of the lead. Each row of directional electrodes includes multiple electrodes arranged circumferentially around the lead body. In one embodiment, there are two rows of three electrodes, and one row of two electrodes, which may be arranged in any order. Thus, the electrode configuration at the distal end may have a "3-2-3", a "2-3-3" or a "3-3-2" configuration.

In another embodiment, a lead has any one of, all of, or any combination of the following features: a cylindrical lead body having a diameter of about 0.70 millimeters (mm) to about 1.5 mm; at least one row of directional electrodes disposed on the outer surface of the cylindrical lead body, wherein each directional electrode spans from about 90° to 120° around the circumference of the body; each directional electrode being radially spaced apart from an adjacent electrode segment by about 30° to 60°; each directional electrode being axially spaced apart from an adjacent electrode by 0.25 mm to 2.00 mm; each directional electrode having a surface area of about 1.5-3 mm$^2$; and each electrode having a length of about 1.5 mm; and at least one unitary electrode having multiple exposed portions on the outer surface, wherein each exposed portion of the unitary electrode spans about 60° to 120° around the circumference of the lead body.

In one embodiment, directional electrodes are held in place with at least one retention ledge, which may be of the same or different material from the electrode. The retention ledge may be defined as a step on an edge of the electrode stimulating surface that is covered by an insulating material, such as, for example, polyurethane or silicone, that locks the electrode in place. The retention ledge or ledges need not encompass the entire perimeter of the electrode edge, and may only be on the distal and proximal edges of the electrode.

In another embodiment, the directional electrode further comprises a retention ledge that defines gaps along one side of the perimeter of the electrode and has a tab on the other side of the perimeter of the electrode. The tab of the radially adjacent electrode fits within the gap such that contact is prevented between the retention ledges of the adjacent electrodes.

In another embodiment, the retention ledge defines holes, mesh, grooves, or voids that allow the insulating material to flow therethrough and further anchor the electrode to the lead body. It is favorable for the electrode to be firmly affixed to the finished lead body so that the electrodes are not inadvertently removed during implant or use.

In one embodiment, the directional electrode are positioned in their respective orientations so that once insulating material is assembled to capture the electrodes, they are aligned in their desired positions. In another embodiment, the electrodes may be affixed to conducting wires prior to positioning. The electrodes are then held in this position by means of a support structure/framework affixed to the outer surface of the electrodes. In one embodiment, the framework is a metal similar to that of the electrodes and is welded to the electrodes. In another embodiment, the framework is plastic and is adhered or molded to the electrodes. In some embodiments, attachment of the framework may require temporary fixturing or scaffolding to hold the electrodes in position with the framework while they are fastened.

In one embodiment, the framework design may be as simple as a rod or wire that is welded to the outer surface of the electrodes. In another embodiment, the framework may be a complex structure such as a wire mesh.

In one embodiment the framed electrodes are slid over an extruded tube that functions as the core of the lead body. Additional insulating material may be added to the spaces in between electrodes by hot reflow of a similar plastic material. In another embodiment, the framed electrodes are held in a mold and insulating material is pressed into the space in between electrodes. During the process of adding insulating material, the material captures the retention features of the electrodes, such as ledges or holes and thereby affixes the electrodes in their desired locations on the lead body.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 2b is a cross-sectional view of the unitary electrode of FIG. 2a.

FIG. 3b is a cross-sectional view of the unitary electrode of FIG. 3a.

FIG. 4b is a cross-sectional view of the unitary electrode of FIG. 4a.

FIG. 5b is a cross-sectional view of the unitary electrode of FIG. 5a.

FIG. 6b is a cross-sectional view of the unitary electrode of FIG. 6a.

FIG. 11b is a plan view of the directional electrode of FIG. 11a.

DETAILED DESCRIPTION

The present invention provides electrical leads comprising a cylindrical lead body having at least one, and preferably, a plurality of directional electrodes disposed on a distal end thereof. Furthermore, in certain embodiments, an electrical lead comprises at least one, and preferably, a plurality of unitary electrodes disposed thereon. As used herein, a "directional electrode" refers to an electrode on a lead body, in which the electrode extends less than 360° about the circumference of the lead body. As used herein a "unitary electrode" refers to an electrode that has at least one portion on the external surface of the lead that is exposed to the environment during use (the external surface of the electrode) and at least one portion covered completely by insulating material, wherein all exposed portions are electrically connected beneath the external surface of the lead such that the unitary electrode is activated as one unit when power is supplied thereto.

Figure 1:
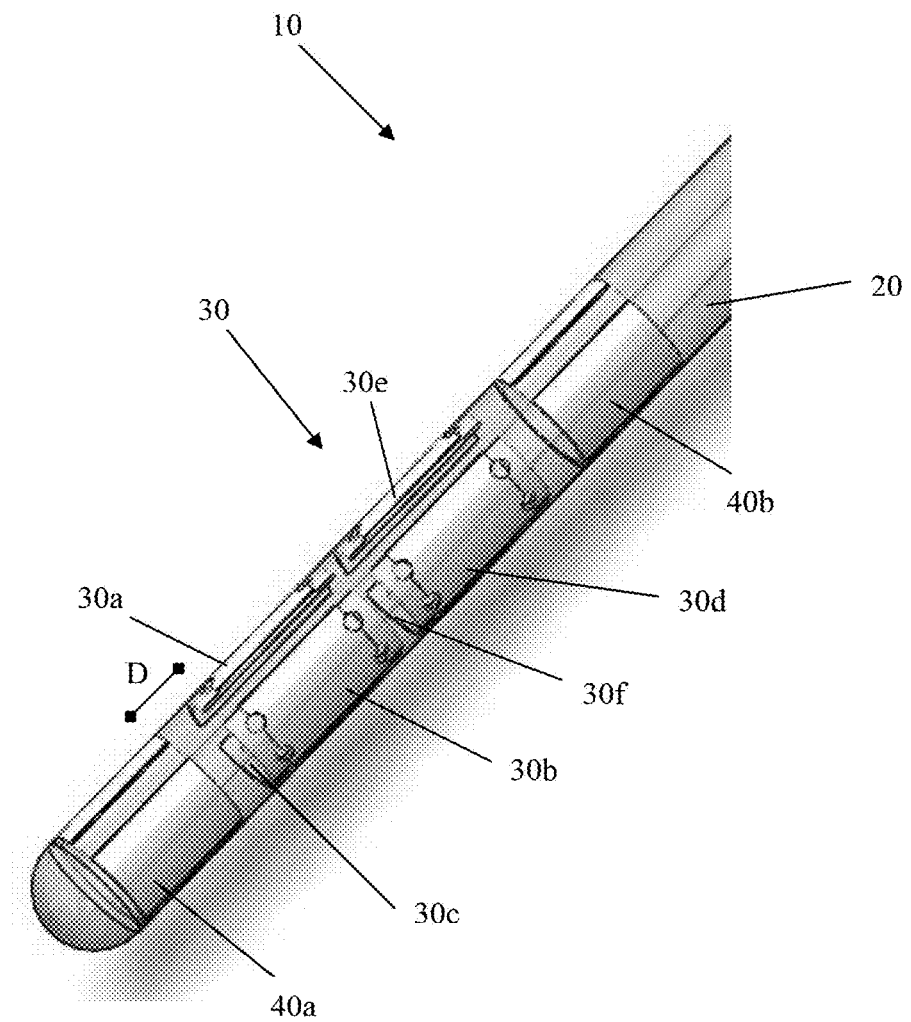
FIG. 1 is a perspective view of a distal end of a lead with directional electrodes and unitary electrodes disposed thereon in a 1-3-3-1 configuration.

FIG. 1 shows an embodiment of electrical lead 10 comprising a cylindrical lead body 20 having a plurality of rows 30 of directional electrodes and a plurality of unitary electrodes 40a, 40b disposed along the longitudinal axis of lead body 20. In FIG. 1, the distalmost electrode 40a and the proximalmost electrode 40b on the distal end of lead body 20 are unitary electrodes and two rows 30 of directional electrodes are located therebetween. In this embodiment, each row 30 of directional electrodes comprises three electrodes arranged circumferentially around the lead. The distal row of directional electrodes is illustrated as comprising electrodes 30a, 30b, and 30c and the proximal row of directional electrodes is illustrated as comprising electrodes 30d, 30e, and 30f.

Figure 2A:
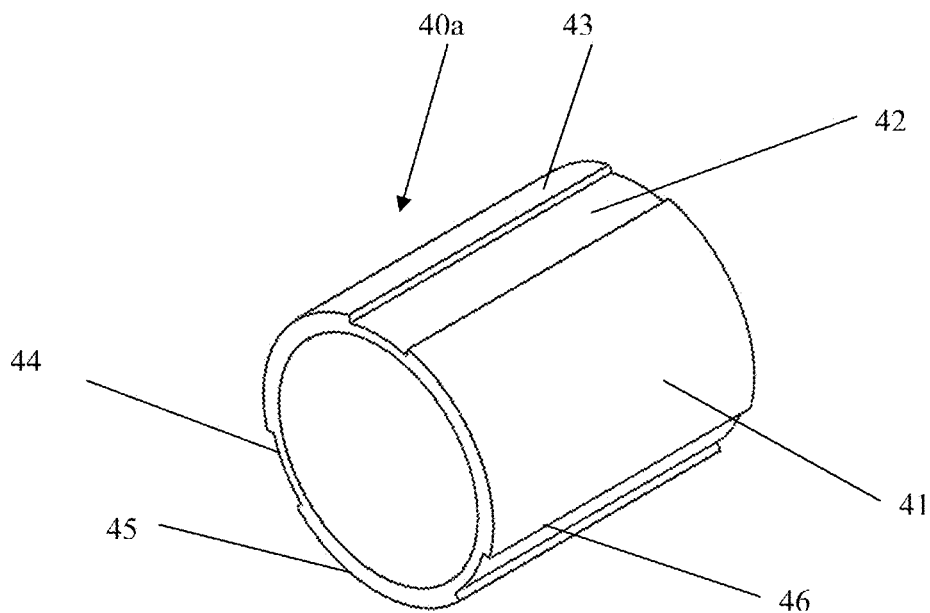
FIG. 2a is a perspective view of an embodiment of a unitary electrode having three raised portions.
Figure 2B:
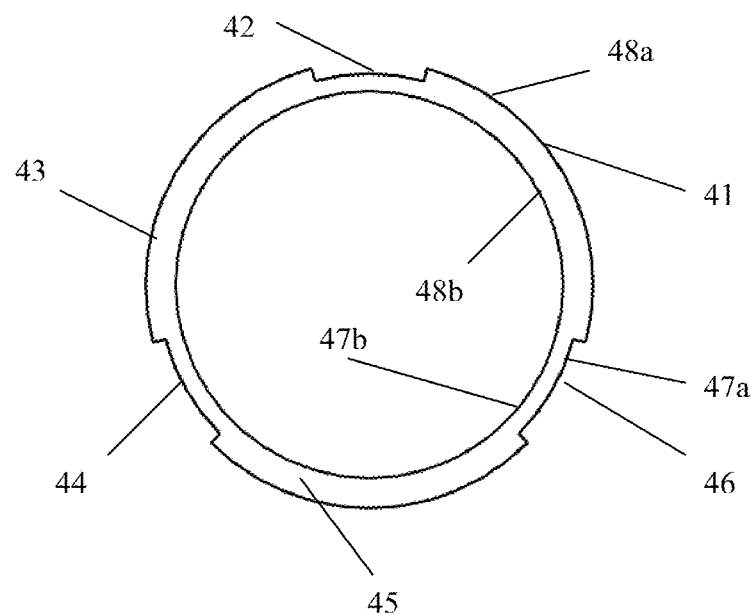

FIGS. 2A and 2B show an embodiment of a unitary electrode 40a in which the at least one portion covered by insulating material is three recessed portions. Specifically, in this embodiment, unitary electrode 40 has three raised portions 41, 43, 45 and three recessed portions 42, 44, 46 located between the raised portions 41, 43, 45, respectively. As seen in FIG. 2B, the recessed portions 42, 44, 46 each have an outer surface 47a that is indented relative to the outer surface 48a of the raised portions, and an inner surface 47b that is continuous with the inner surface 48b of the raised portions, such that the inner surface of the unitary electrode is smooth. Before assembly on the lead, unitary electrode 40 resembles a band electrode in that the electrode material encircles 360 degrees. However, when the unitary electrode 40 is placed on the lead during manufacturing, insulating material flows over the recessed portions 42, 44, 46 completely covering these portions. Thus, after assembly, only the raised portions 41, 43, 45 are exposed to tissue and come in contact with tissue. After assembly on the lead, the unitary electrode resembles a row of three directional electrodes, however all three exposed portions 41, 43, 45 are essentially considered a single electrode, since the three exposed portions are electrically connected together and when activated, will activate together as one electrical circuit In one preferred embodiment, the raised portions 41, 43, 35 of the unitary electrode are longitudinally aligned with the directional electrodes 30a, 30b, 30c, as shown in FIG. 1. This alignment allows for a longitudinal uniform charge distribution when the directional electrode settings are the same, which maintains symmetry in charge distribution and makes it easier to predict what the electrical field will look like when the user is selecting electrodes to activate. However, in an alternative embodiment, the raised portions of the unitary electrodes can be rotated relative to the directional electrodes such that the exposed portions of the unitary electrodes are not aligned with the directional electrodes (i.e. the exposed external surfaces of the unitary electrode and directional electrode are staggered). If a directional electrode serves as a cathode and a unitary electrode serves as an anode, the current will flow longitudinally if all the electrodes are aligned longitudinally as described above. Otherwise, if the directional electrode is not aligned with the exposed external surfaces of the unitary electrode, the current will flow longitudinally with a bias in the direction of the exposed surfaces of the unitary electrode. Accordingly, an embodiment where the unitary electrode exposed surfaces and the directional electrode are not longitudinally aligned may be preferred when the user wants the electrical current to travel longitudinally with some bias around the perimeter of the lead body.

It should be noted that the unitary electrode need not comprise three raised portions and three recessed portions. The unitary electrode can comprise one or more raised portions and one or more recessed portions.

Figure 3A:
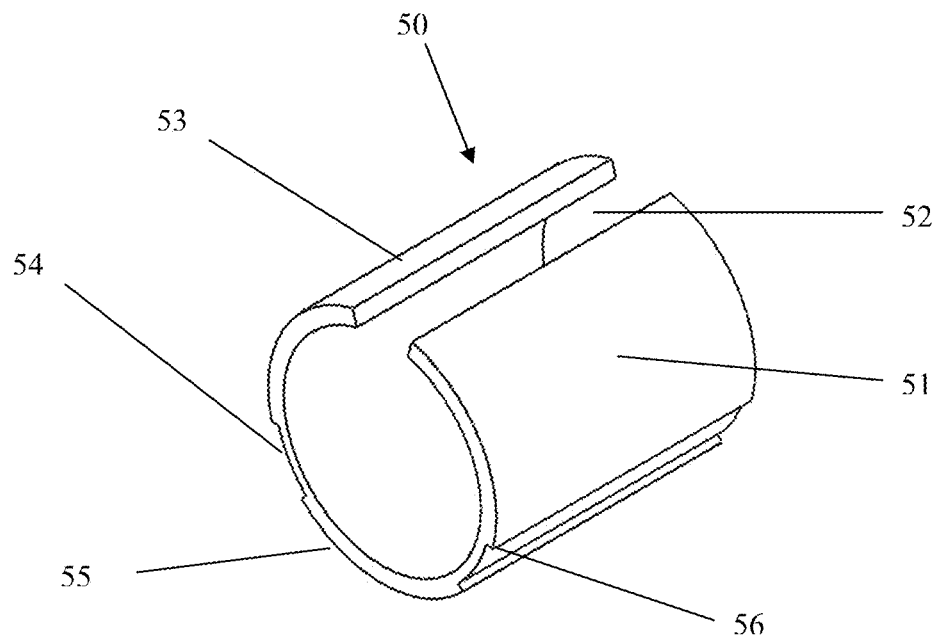
FIG. 3a is a perspective view of another embodiment of a unitary electrode defining a space.
Figure 3B:
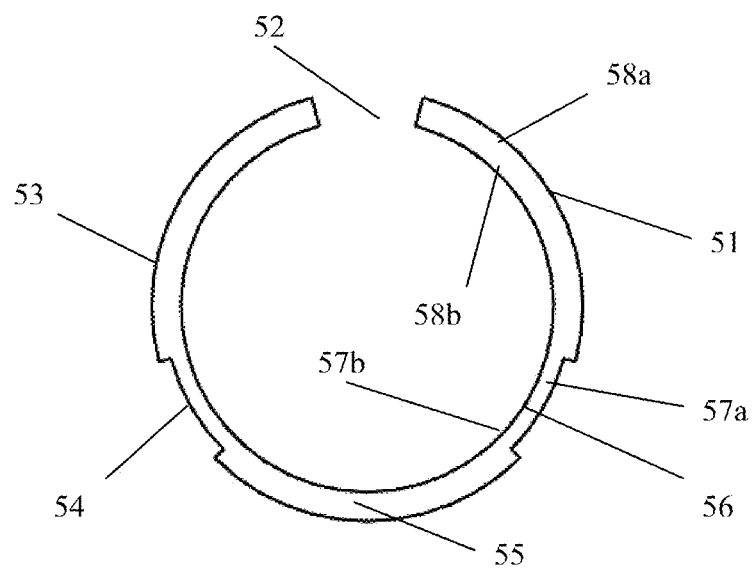

FIGS. 3A and 3B show another embodiment of a unitary electrode 50 in which the at least one portion covered by insulating material is two recessed portions. Similarly to the first embodiment, the unitary electrode 50 has three raised portions 51, 53, 55 but has only two recessed portions 54, 56. As seen in FIG. 3B, the recessed portions 54, 56 each have an outer surface 57a that is indented relative to the outer surface 58a of the raised portions, and an inner surface 57b that is continuous with the inner surface 58b of the raised portions, such that the inner surface of the unitary electrode is smooth. Rather than a third recessed portion, the unitary electrode defines a space 52 between the raised portions 51 and 53. Such a space can be advantageous during manufacturing as the unitary electrode could be stamped or wrapped around the lead or the conductor wire could be welded into the space. Thus, the unitary electrode 50 does not extend a full 360 degrees, but rather forms a C-shape. In one embodiment, the space 52 has a radial span of about 30 degrees and the electrode extends about 330 degrees circumferentially. However, other dimensions for the space 52 are possible. When the unitary electrode 50 is placed on the lead during manufacturing, insulating material flows over the recessed portions 54, 56 completely covering these portions. Thus, after assembly, only the raised portions 51, 53, 55 are exposed and can contact tissue.

Figure 4A:
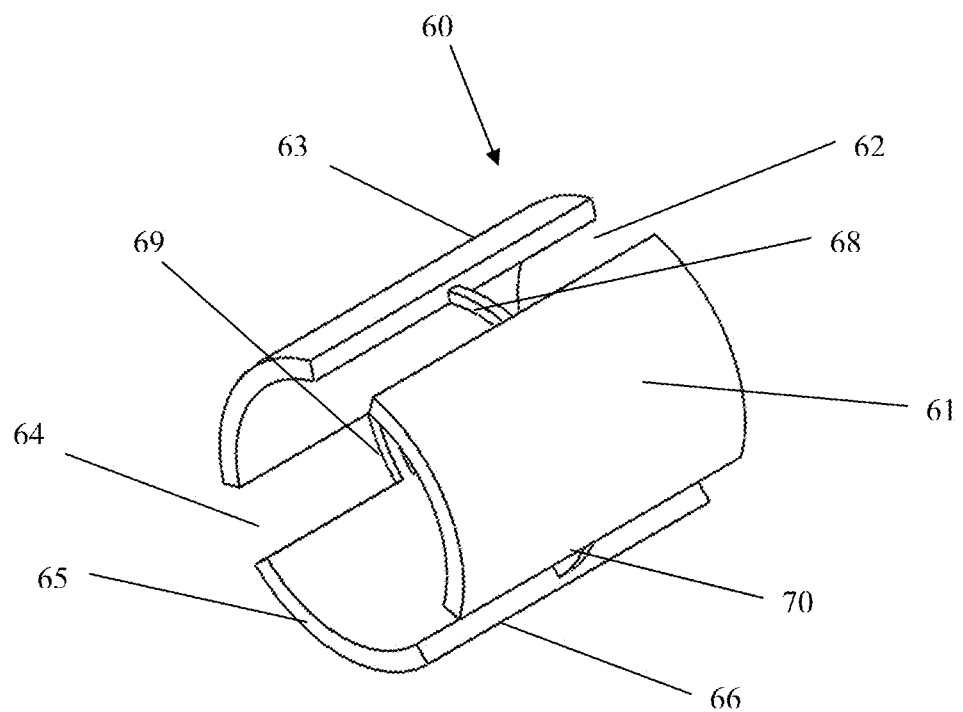
FIG. 4a is a perspective view of another embodiment of a unitary electrode having connectors.
Figure 4B:
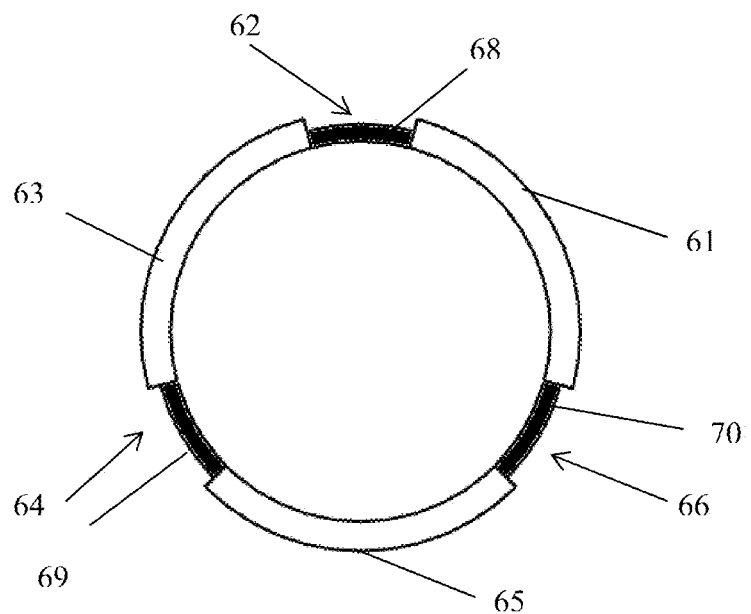

FIGS. 4A and 4B show another embodiment of a unitary electrode 60 in which the at least one portion covered by insulating material comprises three connectors. Similarly to the first embodiment, the unitary electrode 60 has three raised portions 61, 63, 65 but has no recessed portions. There is a gap 62, 64, 66 between each of the raised portions 61, 63, 65. In order for the three raised portions to be activated together, the three raised portions are electrically connected by at least two connectors. For example, the raised portions 61, 63 are connected together by a first connector 68, the raised portions 65 and 63 are connected together by a second connector 69, and the raised portions 61 and 65 are connected together by a third connector 70. Connectors 68, 69, 70 can be electrically conductive wires, tabs, extensions, or any other means by which the raised portions are electrically connected. The connectors 68, 69, 70 are recessed relative to the raised portions such that they can be fully covered by the insulating material during assembly of the lead, as seen in FIG. 4B. In an alternative embodiment, there may only be two connectors. In other words, the unitary electrode need not comprise three raised portions and three connectors. The unitary electrode can comprise two or more raised portions and two or more connectors. When the unitary electrode 60 is placed on the lead during assembly, insulating material flows over the connectors 68, 69, 70 completely covering these portions. Thus, after assembly, only the raised portions 61, 63, 65 are exposed and can contact tissue.

As stated above, although the unitary electrode is described as having three raised portions in exemplary embodiments, there may be any number of raised portions. The unitary electrodes 70, 80 with a single raised portion (described below) have all the benefits of a directional electrode, but can be more easily secured onto the lead body since the electrode can encompass substantially the entire lead body circumference.

Figure 5A:
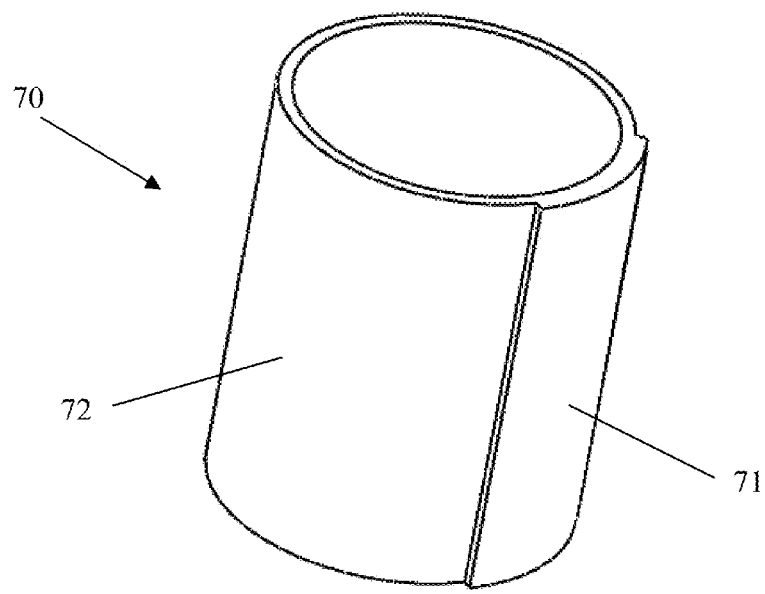
FIG. 5a is perspective view of another embodiment of a unitary electrode having one raised portion.
Figure 5B:
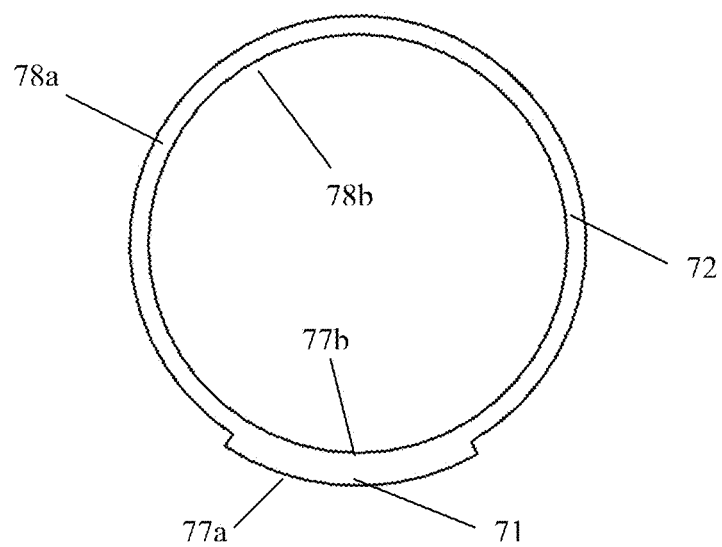

FIGS. 5A and 5B show another embodiment of a unitary electrode 70 having only one raised portion 71. Although the unitary electrode is illustrated as having a radial span of 360 degrees, alternatively the unitary electrode could have a radial span of between 270 and 360 degrees, or a radial span of less than 270 degrees. The single raised portion 71 preferably has a radial span of 30-120 degrees, with the remaining portion 72 of the electrode being recessed relative to the raised portion and thus covered by insulating material during assembly. As seen in FIG. 5B, the raised portion 71 has an outer surface 77a that is raised relative to the outer surface 78a of the remaining portion 72, and an inner surface 77b that is continuous with the inner surface 78b of the remaining portion 72, such that the inner surface of the unitary electrode is smooth. Although the raised portion 71 is illustrated as being rectangular, any suitable shape is possible.

Figure 6A:
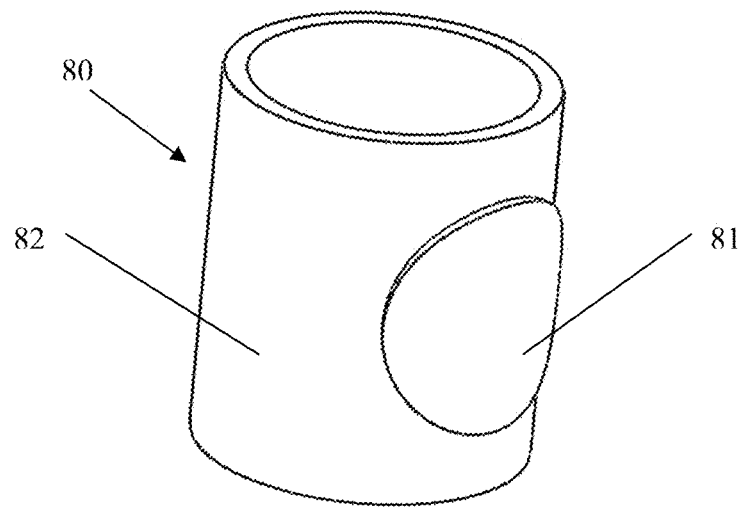
FIG. 6a is a perspective view of an embodiment of a unitary electrode having one circular raised portion.
Figure 6B:
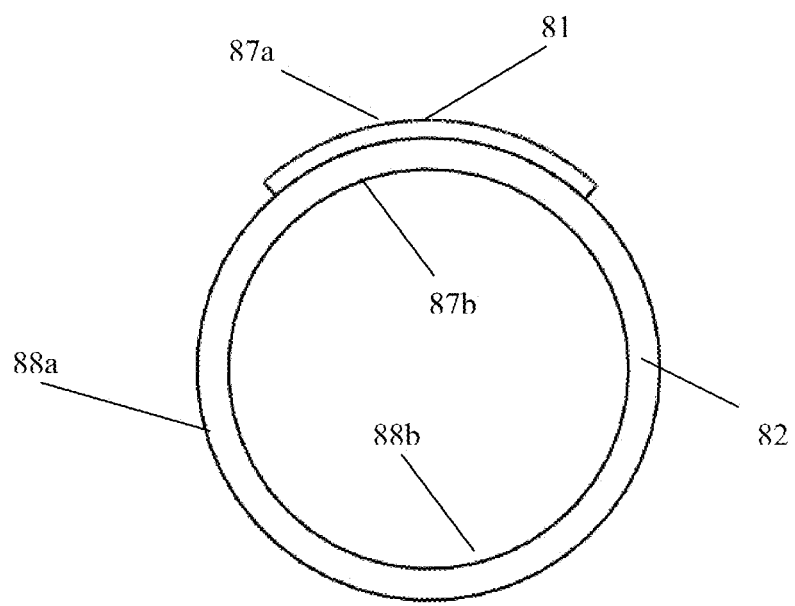

FIGS. 6A and 6B show another embodiment of a unitary electrode 80 having a circular raised portion. The unitary electrode 80 may include a single raised portion 81 that does not extend the full length or circumference of the electrode, such as a circular raised portion 81, to more closely target a specific region. The raised portion 81 can be any size or shape, with the remaining portion 82 of the electrode being recessed relative to the raised portion and thus covered by insulating material during assembly. As seen in FIG. 6B, the raised portion 81 has an outer surface 87a that is raised relative to the outer surface 88a of the remaining portion 82, and an inner surface 87b that is continuous with the inner surface 88b of the remaining portion 82, such that the inner surface of the unitary electrode is smooth.

Figure 7:
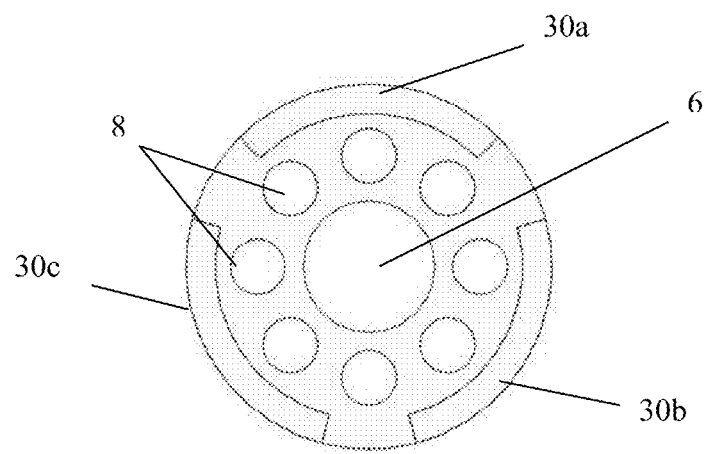
FIG. 7 is a cross-sectional view of a row of three circumferential directional electrodes showing also the lumens for the conductor wires that pass through the body of the lead.

FIG. 7 is a cross-sectional view of a lead, showing row 30 of three directional electrodes as well as lumens for conductor wires that connect to the electrodes. The row of directional electrodes does not form a continuous electrode surface, but rather the electrode surface is segmented into a plurality of individual electrodes that are electrically isolated from each other. Individual directional electrodes can range in an angular distance around the exterior of the body of the elongate lead by as little as a few degrees to almost completely around the body of the lead. FIG. 7 shows one embodiment in which each of the directional electrodes 30a-c are curved around the cylindrical body 20 so that the electrodes each have a radial span of approximately 90° about the circumference of the lead body 20 and each electrode is radially spaced apart from an adjacent electrode by about 30°. Also shown in FIG. 7 are eight lumens 8 for receiving conductors from each electrode and a central lumen 6 for receiving a stylet or other instrumentation. An additional row 30 of directional electrodes 30d-f can have a similar radial span and radial spacing. Of course other configurations for the radial span and radial spacing of the electrodes are also contemplated. Although only two rows 30 of directional electrodes are shown in FIG. 1, multiple rows are contemplated. Further, each row is shown as including only three electrodes but a row of electrodes can include more or less than three electrodes (such as two electrodes). In a preferred embodiment, the directional electrodes in adjacent rows are aligned with each other with respect to the longitudinal axis of the lead body, however they could alternatively be rotated relative to each other.

Figure 8:
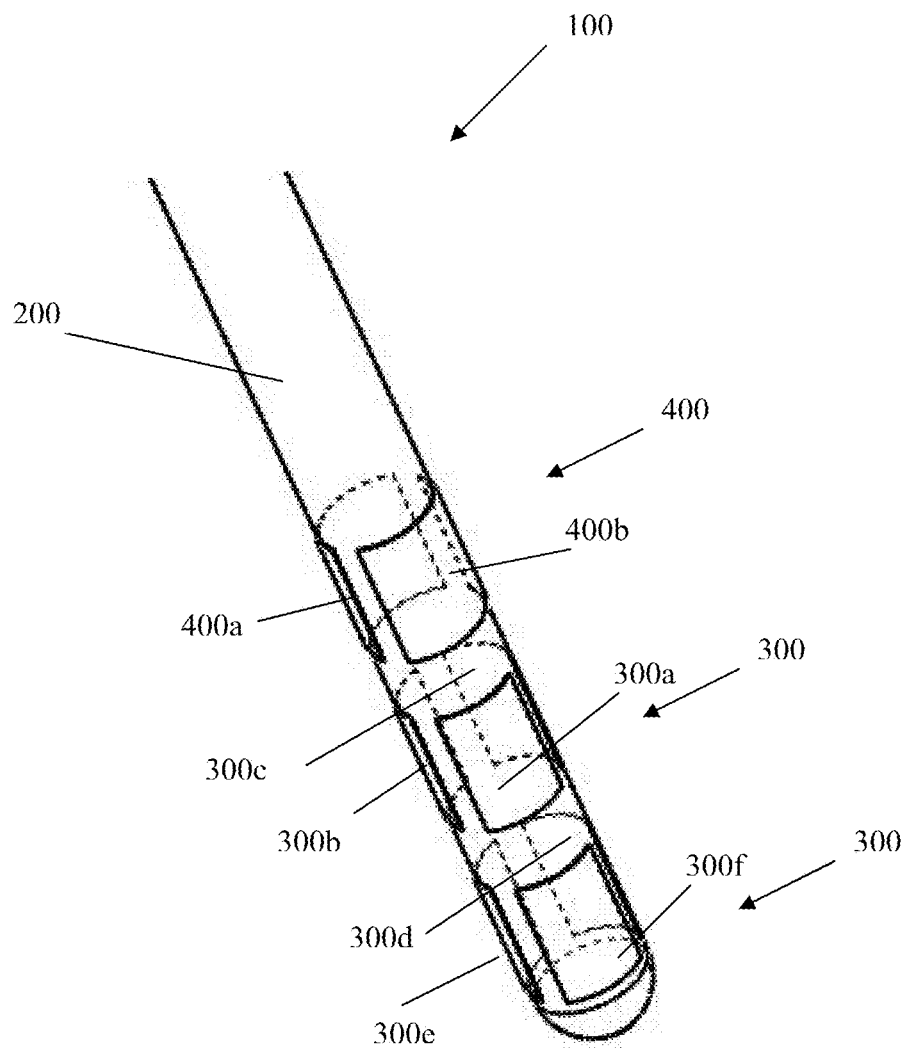
FIG. 8 is a perspective view of a distal end of a lead with directional electrodes thereon in a 2-3-3 configuration.
Figure 9:
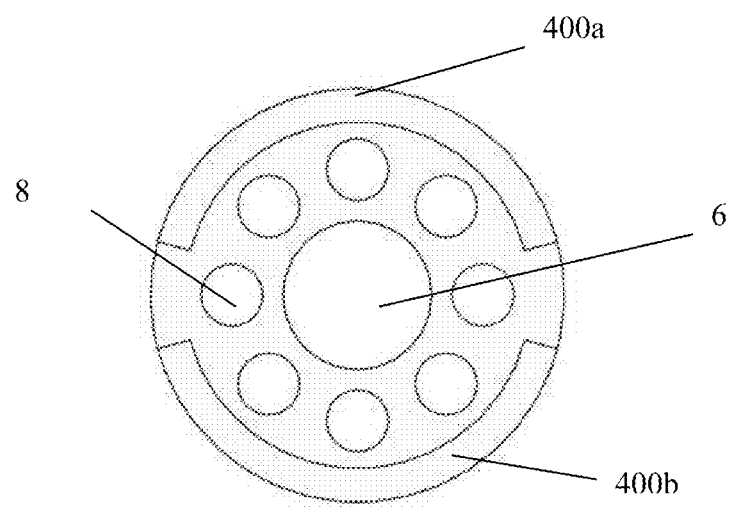
FIG. 9 is a cross-sectional view of a row of two circumferential directional electrodes showing also the lumens for the conductor wires that pass through the body of the lead.

FIG. 8 shows an alternative embodiment of electrical lead 100 comprising a cylindrical lead body 200 having a plurality of rows of directional electrodes along the longitudinal axis of the lead body 200. Two rows 300 of directional electrodes comprise three electrodes 300a-c and 300d-f, respectively, arranged circumferentially about the lead body and one row 400 of directional electrodes comprises two electrodes 400a, 400b arranged circumferentially about the lead body. As can be seen in the cross-sectional view of FIG. 9, the electrodes 400a, 400b can each have a radial span of about 120 degrees and a radial spacing of about 60 degrees between them. The electrodes 300a-f, similarly to electrode 30a-f described above, can each have a radial span of about 90 degrees and a radial spacing of about 30 degrees between them.

One consideration when manufacturing a lead with directional electrodes is to prevent the directional electrodes from becoming detached from the lead body during use. One advantage of a directional electrode with ledges as disclosed herein is that it requires no additional space underneath its inner surface for tabs or other retention mechanisms. In some embodiments, it may be desirable to create holes, mesh or channels in the ledge as described below to provide sufficient holding force to prevent the directional electrode from becoming detached from the lead body, especially if the lead body is subject to flexure. Insulating material may be assembled in a variety of methods, such as reflow or injection molding over the retention ledge, through the hole(s) in the retention ledge, and underneath the retention ledge. Thus at least a portion of the electrode is enveloped by insulation material, creating a positive lock to prevent the electrode from detaching from the lead body.

Figure 10:
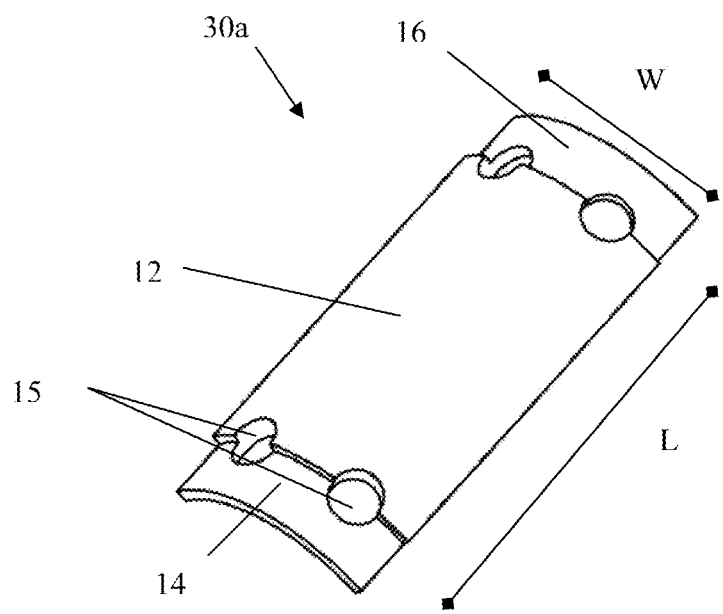
FIG. 10 is a perspective view of an embodiment of a directional electrode having retention ledges defining anchoring holes therethrough.

FIG. 10 shows an embodiment of a directional electrode 30a with retention ledges and optional anchoring holes. In this embodiment, the electrode includes an exposed electrical surface or raised portion 12 and retention ledges 14, 16. The retention ledges are located at the distal edge and the proximal edge of electrode 30a. In this embodiment, electrode 30a also includes optional anchoring holes 15 therethrough which are defined by raised portion 12 and retention ledges 14, 16. Each anchoring hole can have a diameter, for example, between 0.001" to 0.020." FIG. 10 shows two holes 15 mutually defined by the proximal edge of raised portion 12 and the distal edge of retention ledge 16 and two holes 15 mutually defined by the distal edge portion of raised surface 12 and the proximal edge of retention ledge 14. The retention ledges 14, 16 and the holes 15 act to hold the directional electrode in place on the lead. When the lead is assembled, insulating material flows over and fully covers retention ledges 14, 16 and flows into and through holes 15. The invention is not limited to the number, shape, size, or location of the holes so long as the holes contribute to securing the directional electrodes to the lead body during manufacture. In addition, as shown in this embodiment a hole may overlap with the raised surface 12 of the electrode, and is not constrained to being defined entirely by the retention ledge or the raised portion of the electrode. Other embodiments may include slots, square holes, stepped or angled holes, or multiple holes such that the ledge may be considered a mesh surface.

Figure 11A:
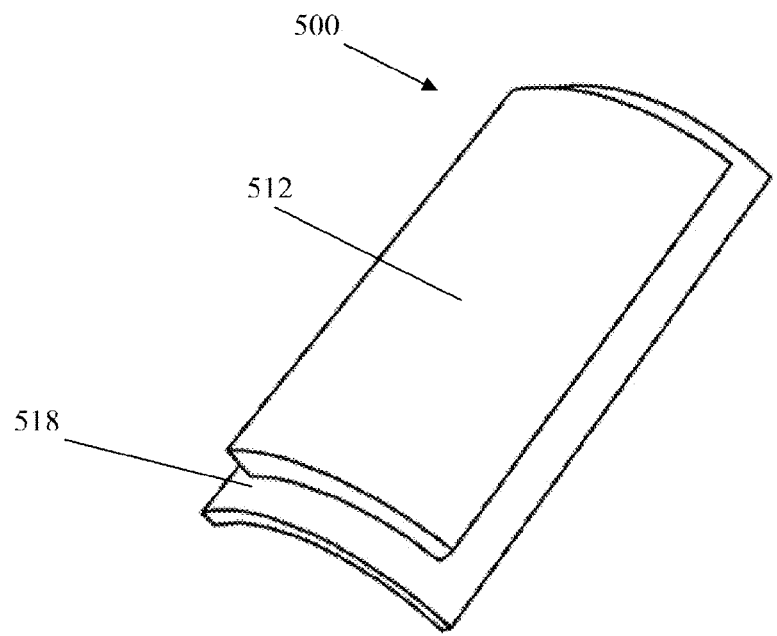
FIG. 11a is a perspective view of another embodiment of a directional electrode having retention edges around the entire perimeter.
Figure 11B:
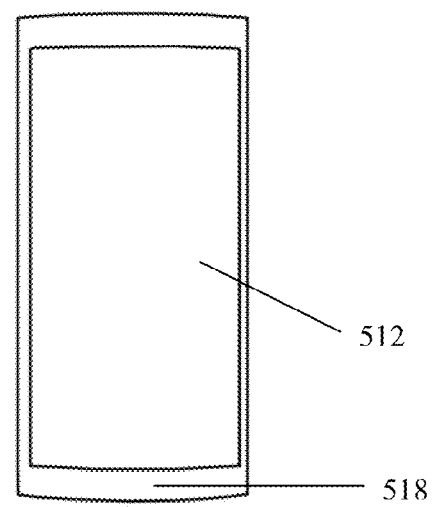

FIGS. 11A and 11B illustrate another embodiment of a directional electrode 500. Directional electrode 500 includes an exposed electrical surface or raised portion 512 and a retention ledge 518 extending around the periphery of the raised portion 512. The retention ledge 518 need not be electrically conductive, but may be machined as a feature on the electrode for manufacturing simplicity. The ledge depth and width may be determined by the particular stresses and forces of the specific application to which the lead body may be subjected. The ledge depth may determine the thickness of insulating material that will cover the retention ledge to hold it in place. In this embodiment, the ledge 518 extends around the entire perimeter of the exposed electrical surface as illustrated in FIG. 11B, although the ledge need only extend along one edge, or part of an edge. The raised portion 512 has an outer surface that is raised relative to the outer surface of the retention ledge 518, and an inner surface that is continuous with the inner surface of the retention ledge, such that the inner surface of the unitary electrode is smooth. In this embodiment the outermost surface of the raised portion 512 is contoured to have a radius equal to the radius of the outer surface of the lead body, and the retention ledge 518 surface is contoured to form an arc parallel to the outer surface of the raised portion. It is not necessary that the retention ledge be parallel to the raised portion, but it may be desirable to form an even covering of insulating material. In other embodiments, there may be multiple grooves or holes in the retention ledge, in which case the retention ledge does not form a parallel contour.

Figure 12:
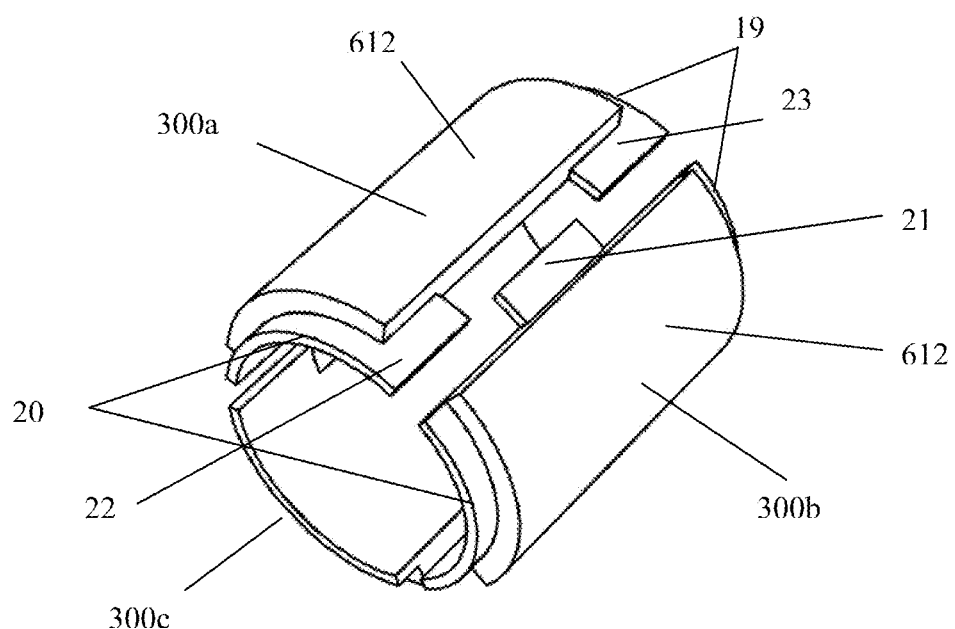
FIG. 12 is a perspective view of another embodiment of a directional electrode having retention ledges defining a gap on one side and having a tab on the other side.

In FIG. 12, another embodiment of three directional electrodes are illustrated as they may be assembled onto a lead assembly, with the lead body, conductors, and other components not shown in this view. In such an embodiment, three directional electrodes 300a, 300b, 300c may be assembled radially onto a lead body 100 in order to produce stimulation that may be directed radially. In an embodiment, electrode 300a includes a raised portion 612 and retention ledge, such as a proximal ledge 19 and a distal ledge 20, and the adjacent electrode 300b includes a raised portion 612 and retention ledges that include radial tab 21. The distal ledge 20 has a distal radial portion 22 that extends radially towards the adjacent electrode 300b, and the proximal ledge 19 has a proximal radial portion 23 that extends radially towards the adjacent electrode 300b. The proximal radial portion 23 and the distal radial portion 22 define a central gap therebetween which receives radial tab 21 of adjacent electrode 300b. This staggering of the ledge portions and the radial tab to accommodate the tight radial spacing in between electrodes assures that the adjacent directional electrodes are held securely on the lead but are not in electrical contact with each other. Although not seen in this figure, the hidden left side of electrode 300a includes a radial tab, similar to that of electrode 300b. Additionally, although not seen in this figure, the hidden right side of electrode 300b includes a proximal radial portion and a distal radial portion similar to electrode 300a. The higher the voltage used in stimulation, the more space that may be required between electrodes (or between the ledges if they are made of electrically conductive material) to avoid arc currents between adjacent electrodes.

Figure 13:
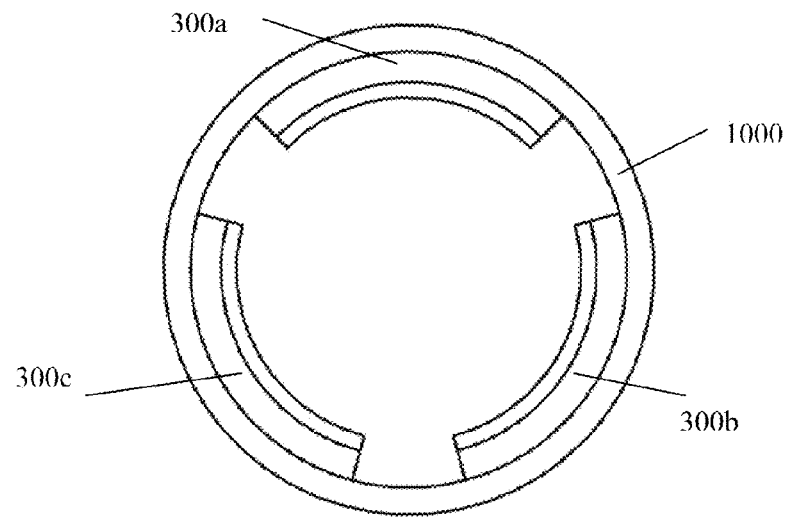
FIG. 13 is a cross-sectional view of a support structure with three circumferential electrodes for mounting the electrodes to a lead body.
Figure 14:
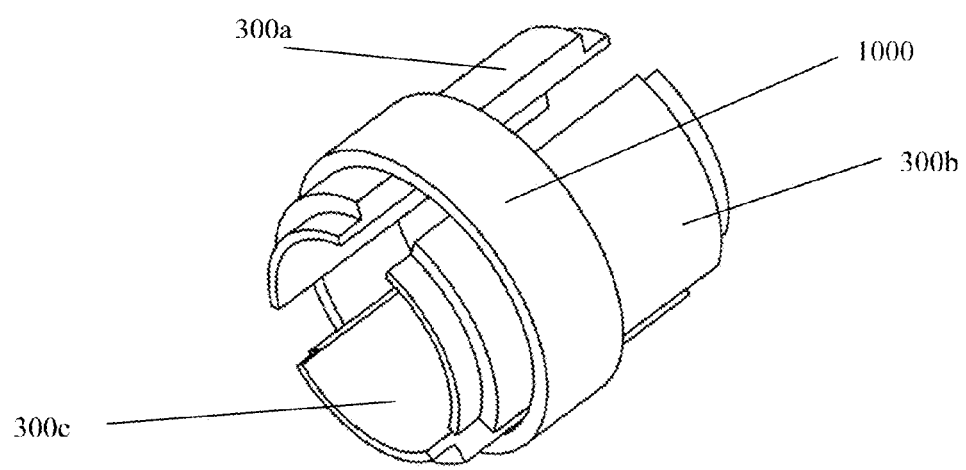
FIG. 14 is a perspective view of the support structure and three circumferential electrodes of FIG. 13.

In another embodiment, the space between electrodes may be reduced by removing radial portions of the ledges completely as illustrated in FIG. 13. In some embodiments, the electrodes may be held together by a support structure, such as the ring 1000 shown in FIGS. 13 and 14. In such an embodiment the desired spacing is held while insulating material is added. After the insulating material is added over the retention ledges the support structure may be removed, leaving the insulating material interlocked with the electrode retention ledges.

The support structure is a temporary assembly feature and is removed from the lead and electrodes after the insulating material has been assembled to sufficiently hold the electrodes in place to complete the lead assembly. In one embodiment the framework is a conductive metal, and therefore must be removed in order to maintain electrical separation between individual partial electrodes. In another embodiment, the framework is a plastic such as PEEK, and must be removed from the electrodes and lead because it protrudes outward from the desired outer surface of the finished lead. In one embodiment the framework and any extra material may be removed by use of centerless grinding techniques in the case of a cylindrical finished lead body. In another embodiment, the framework may be removed by laser, chemical, machining or any other destructive means recognized by one skilled in the art.

Figure 15:
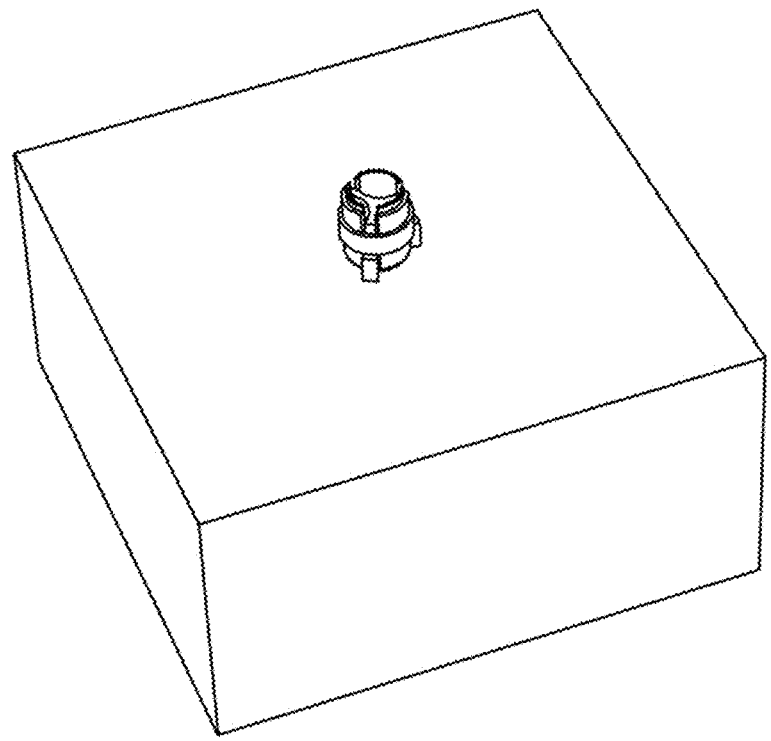
FIG. 15 is a perspective view of a fixture that may be used to position and assemble partial electrodes into a temporary support structure.
Figure 16:
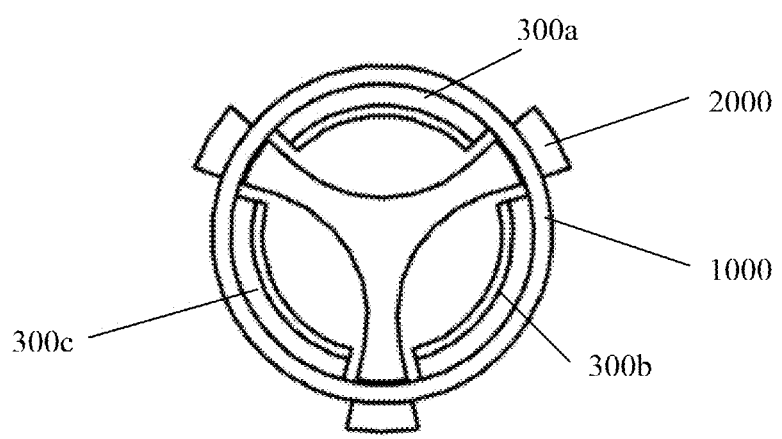
FIG. 16 is a top view of the fixture of FIG. 15.
Figure 17:
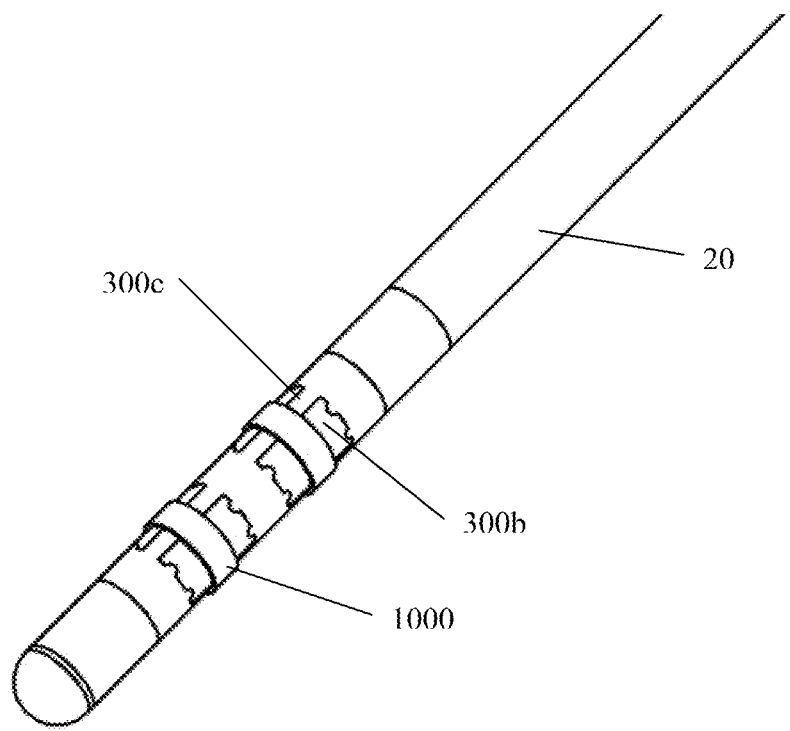
FIG. 17 is a perspective view of the electrodes and the support structure assembled onto a lead body.
Figure 18:
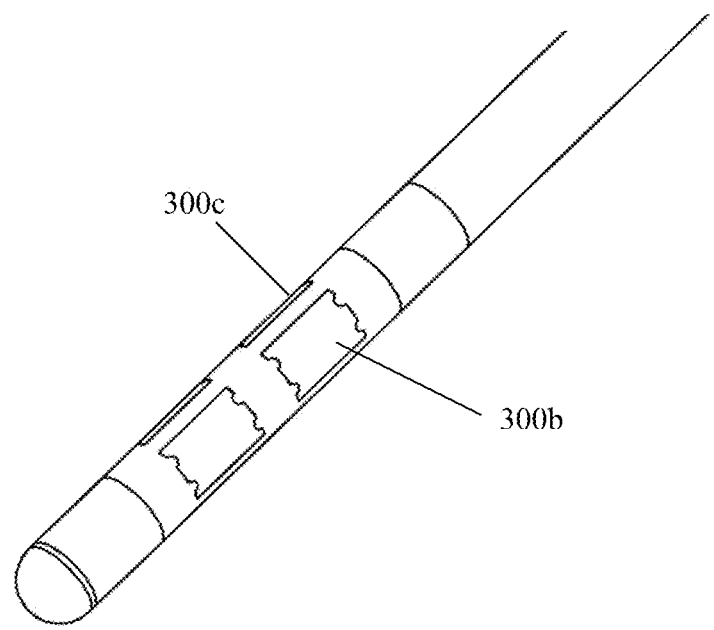
FIG. 18 is a perspective view of the lead of FIG. 17 with the support structure removed.
Figure 19:
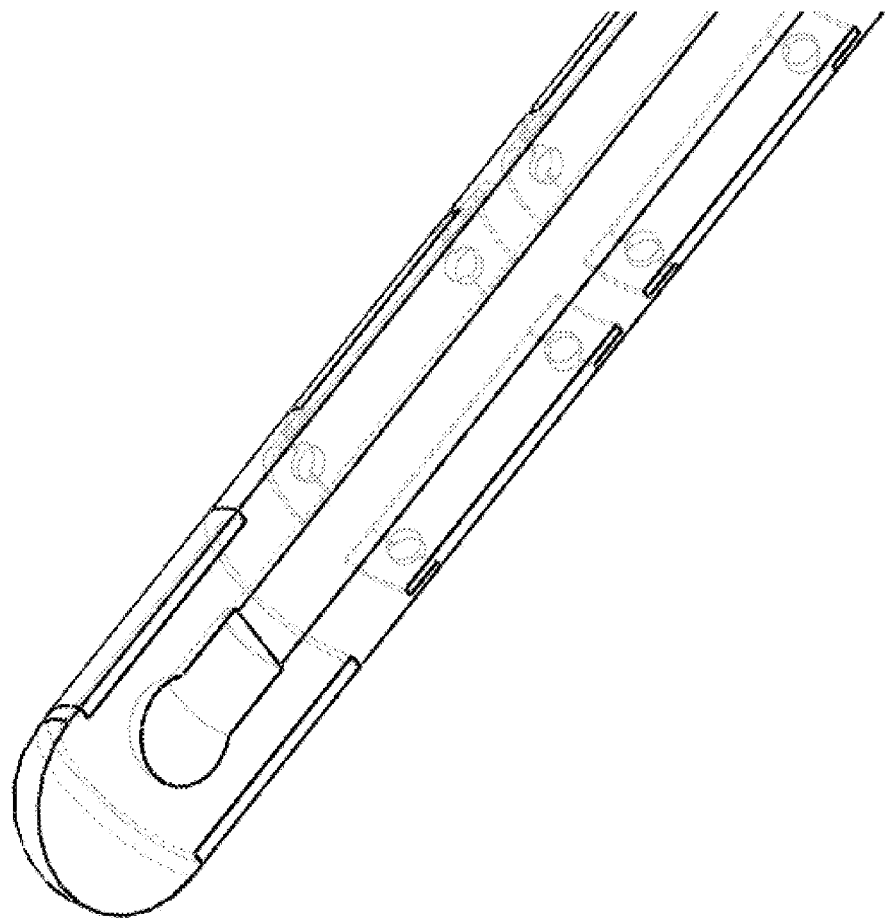
FIG. 19 is a perspective cross-section of a lead assembly with partial electrodes attached to the lead body
Figure 20:
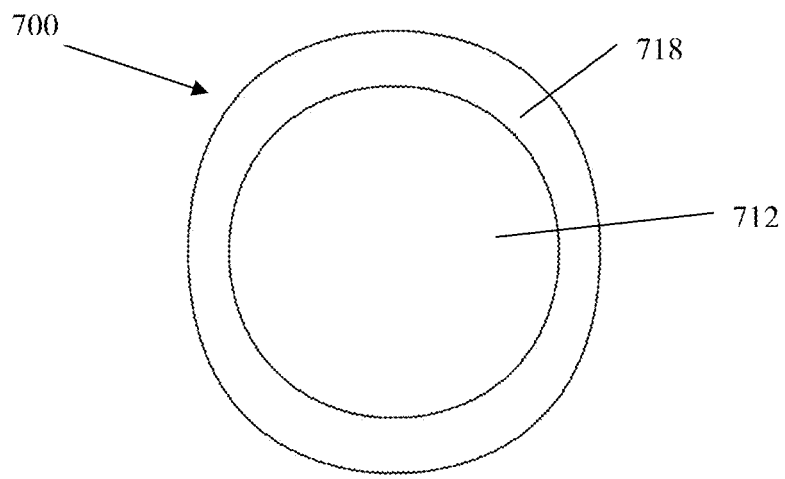
FIG. 20 is a view of the stimulating face of a round electrode that may be assembled onto a lead in another embodiment of the present invention.
Figure 24:
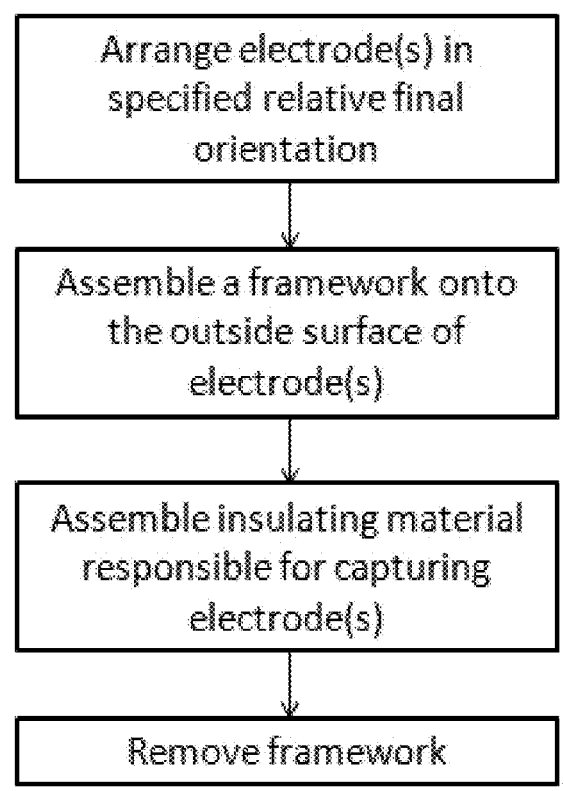
FIG. 24 is a flow diagram of a manufacturing method described in the present invention.

FIGS. 15 and 16 show a fixture, such as Y-shaped fixture 2000, can be used to properly position the electrodes 300a, 300b, 300c in the temporary support structure 1000. Then the electrodes assembled together with the support structure 1000 are placed onto the lead 20, as shown in FIG. 17. During assembly, the insulating material flows both over the retention ledges, under the retention ledges, and through the holes (in embodiments with anchoring holes) in the electrode to provide a positive lock around the electrode. Only the raised portions of the electrodes intended to be stimulating surface are exposed, and the retention ledges are not clearly visible since they are covered by insulating material. After the electrodes are mounted to the lead, the support structure is removed, as shown in FIG. 18. FIG. 24 describes the method of assembling the electrodes.

Figure 21:
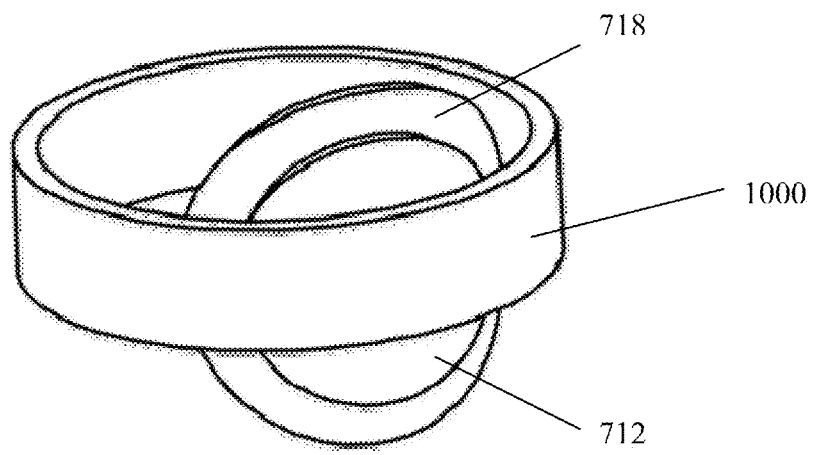
FIG. 21 is a perspective view of the round electrode of FIG. 20 with a support structure attached for anchoring the electrode to the lead body using a manufacturing method of the present invention.
Figure 22:
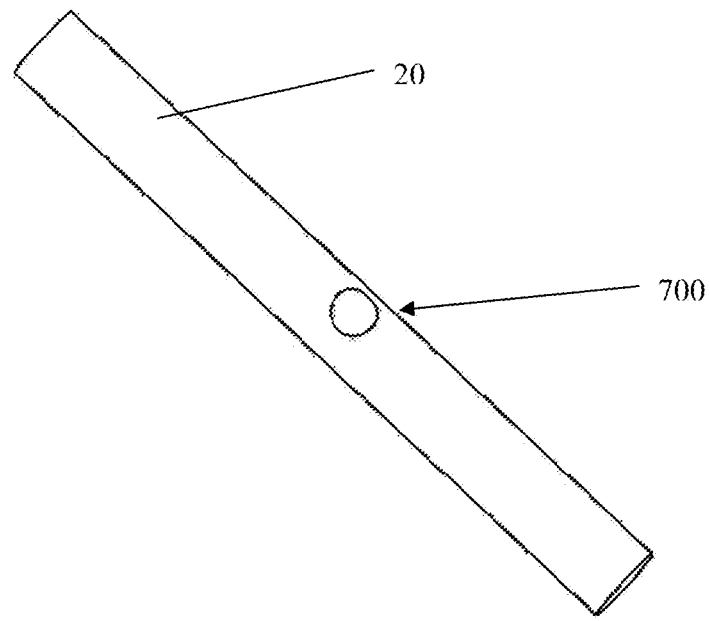
FIG. 22 is a perspective view of a partial completed lead body with the round electrode of FIG. 20 assembled into position on the surface of the lead body FIG. 23 a perspective view of another embodiment of two round electrode with a support structure attached for anchoring the electrodes to the lead body using a manufacturing method of the present invention.
Figure 23:
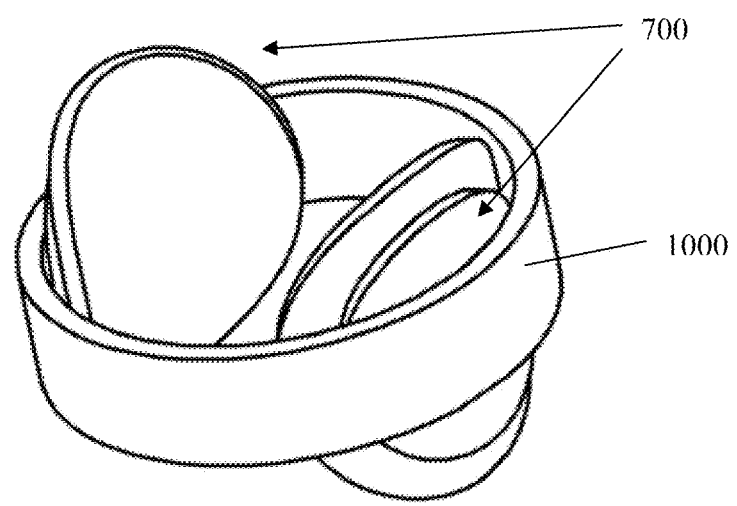

FIGS. 20-23 show an embodiment with round or circular shaped electrode 700. Similarly to the directional electrode 500 of FIGS. 11A and 11B, directional electrode 700 includes an exposed electrical surface or raised portion 712 and a retention ledge 718 extending around the periphery of the raised portion 712. FIG. 21 shows the circular electrode 700 attached to support structure 1000. FIG. 22 shows the circular electrode 700 mounted on lead body 20. FIG. 23 shows an embodiment with two circular electrodes 700 attached to support structure 1000.

Embodiments of the invention may depend upon the size of the electrodes and electrode spacing used in the particular lead assembly. For example, if the radial spacing between directional electrodes is close, there may not be enough space to have ledges on the electrode radial edges without making electrical contact. In such an embodiment, staggered ledges or ledges constrained to the distal and proximal edges may be used in the lead assembly. In another embodiment, it may be desirable to use an insulating material with a more flexible durometer. In such an embodiment, it may be desirable to add anchoring holes to the ledges to create an area of insulating material that extends through the holes, bonds to insulating material underneath the electrode, and creates interlocking fixation of the electrode onto the lead assembly. In one embodiment, insulating material such as epoxies or adhesives may be free-flowed into these holes. In another embodiment, insulating material is potted, molded, or reflowed into the holes.

Additionally, the directional electrodes need not be constrained to shapes that are cylindrical slices. Retention ledges may be utilized around the edges of an electrode surface of any suitable shape that is exposed to the outer surface of the lead body assembly.

In any of the embodiments described above, the size, shape, configuration, and dimensions of the elongate lead will vary depending upon the particular application. For example, the shape of the elongate lead may be cylindrical, flat, conical, etc. Where the elongate lead is cylindrical, the cylindrical lead body preferably has a diameter of about 0.70 mm to 1.5 mm. In a preferred embodiment, the cylindrical lead body has a diameter of about 1.3 mm. Other diameters are also possible, depending, for example, upon the particular application.

Further, the material composition; electrical properties (e.g., impedance); dimensions and configurations (such as, for example, height, width, axial spacing, and shape); number; and arrangement of the stimulation electrodes on the elongate lead will vary depending upon the particular application. For example, the electrodes may have an oval shape, or a rectangular shape. In fact, the individual electrodes may take any variety of shapes to produce the desired focused and/or directional electric field.

Regarding the number of electrodes, in certain embodiments, the cylindrical body has four to twelve electrodes disposed thereon. In a preferred embodiment, the cylindrical body has eight electrodes disposed thereon. The cylindrical lead body could also have other numbers of electrodes disposed thereon.

As denoted in FIG. 10, one embodiment, the directional electrode is approximately rectangular, having two length sides, each with a length L, and two width sides, each with a width W, which is also referred to herein as the "radial spanning." The length sides are approximately parallel to the longitudinal axis of the cylindrical lead body and the width sides are approximately perpendicular to the longitudinal axis of the cylindrical lead body. In certain embodiments, the length of each electrode is about 0.75 mm to 3.0 mm. In a preferred embodiment, the length of the electrode is about 1.5 mm. Of course, the electrodes could also have other dimensions. In certain embodiments, the surface area of each directional electrode is between about 1 $mm^2$ to 3 $mm^2$ and the exposed surface area of each unitary electrode is 4-6 $mm^2$. In a preferred embodiment, the surface area of each directional electrode is about 1.5 $mm^2$ and the exposed surface area of the unitary electrode is 4.5 $mm^2$. In other particularly preferred embodiments, all the directional electrodes have the same surface area irrespective of the particular shape or configuration of the electrode. Of course, it is understood that each directional electrode does not need to have the same surface area and certain electrodes can have different surface areas.

Regarding the axial spacing of the electrodes, in certain embodiments, the plurality of electrodes are spaced along the longitudinal axis at a distance D, as denoted in FIG. 1, of 0.25 mm to 2.0 mm from the next adjacent electrode. In a preferred embodiment, the distance D is about 0.5 mm. Other configurations for the axial spacing between adjacent electrodes is also contemplated. The electrodes can each be longitudinally spaced the same distance apart or the distance between the electrodes can be varied.

The material composition and mechanical properties (i.e. the flexibility) of the body of the elongate lead will vary depending upon the particular application. In some cases, the body of the elongate body is formed of a non-conductive material, such as a polymeric material, glass, quartz or silicone. In a preferred embodiment, the elongate lead is fabricated from polyurethane.

The electrodes can be fabricated from a number of suitable materials including platinum or titanium. In a preferred embodiment, the electrodes are fabricated from platinum iridium.

An electrical lead 10 can be implanted or inserted and removed to modulate specific regions of the body. In certain embodiments, the modulation includes ablation, stimulation and/or inhibition of certain regions of the body. In a preferred embodiment, an electrical lead is used to modulate a part of the nervous system, including the brain, spinal cord, and nerves (including cranial nerves, spinal nerves, and peripheral nerves such as sympathetic and parasympathetic nerves). In a more preferred embodiment, an electrical lead is used to modulate the brain.

Depending on the particular therapeutic application, different electrodes and/or different combinations of electrodes on an electrical lead can be activated to provide different directional modulation of neural tissue, such as specific regions of the brain.

Electrodes of the present invention can have adjustable power. For example, the pulsing parameters of the electrodes may be adjusted to initiate, stop, increase, or decrease the pole combinations, energy, amplitude, pulse width, waveform shape, frequency, and/or voltage or any other pulsing parameter known to one of skill in the art to adjust the degree of modulation delivered thereby. In a preferred embodiment, each electrode of the body of the lead is selectively controllable such that the pulsing parameters of an electrode can be adjusted independent of the pulsing parameters of another electrode.

As will be understood by one of skill in the art, the independent control of each electrode also provides a practitioner with another means of modify or steer the direction of stimulation since the locus of modulation can be selectively adjusted to precisely target portions of the brain to achieve the desired therapy. For example, one electrode may be powered to modulate an area adjacent thereto while the signal to another electrode may be substantially minimized to reduce or stop modulation to an area adjacent to that another electrode. Because the locus of modulation can be selectively adjusted and/or steered in this embodiment of a lead, specific target areas can be precisely targeted to achieve the desired therapy. Other or additional means of selectively steering electrical modulation may also be utilized in the present invention, such as the methods described in U.S. Pat. No. 5,713,922, which is incorporated by reference herein.

The leads of the present invention can be used to treat a variety of medical conditions such as, for example, chronic pain, psychiatric disorders, traumatic brain injury, stroke and the present invention provides for such methods. For example, in certain embodiments a method of treating a medical condition comprises inserting or implanting an electrical lead according to an embodiment of the present invention in a target site of the body and selectively activating one or more of the directional electrodes to provide targeted stimulation of the target site. Specific exemplary target sites includes the cerebellum, basal ganglia, the subthalamic nucleus, the thalamus, and the globus pallidus internus.

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

We claim:

1. An electrical lead comprising:
a cylindrical lead body including an outer surface, a proximal end, a distal end, and a longitudinal axis extending therethrough; and
a unitary electrode that is disposed along the longitudinal axis of the body, wherein:
an outer surface of the unitary electrode is stepped forming a plurality of raised sections and at least one recessed section;
at least one of (a) an inner surface of the unitary electrode, opposite the outer surface, is smooth, and (b) the at least one recessed section is integrally formed with the plurality of raised sections; and
at least one of (a) beneath the outer surface of the lead, a radial span of the unitary electrode is 330 degrees; and (b) a face of at least one of the raised sections is circular.

2. The electrical lead of claim 1, further comprising:
an insulating material covering the at least one recessed section, wherein the plurality of raised sections are exposed surfaces of the electrical lead which are electrically connected to each other via the at least one recessed section.

3. The electrical lead of claim 1, wherein the plurality of raised sections comprises three raised sections.

4. The electrical lead of claim 3, wherein the three raised sections have a cumulative radial span of about 270 degrees.

5. The electrical lead of claim 1, wherein the unitary electrode has a radial span of 360 degrees beneath the outer surface of the lead.

6. The electrical lead of claim 1, wherein beneath the outer surface of the lead, the radial span of the unitary electrode is 330 degrees.

7. The electrical lead of claim 1, wherein the at least one recessed section includes-a plurality of recessed sections located between the raised sections.

8. The electrical lead of claim 7, wherein said plurality of recessed sections are completely covered by an insulating material.

9. The electrical lead of claim 1, wherein the at least one recessed section electrically connects all of the raised sections, the raised sections are exposed, and the electrical lead is configured to perform an electrical stimulation by emitting electrical pulses from the raised sections.

10. The electrical lead of claim 9, wherein said at least one recessed section is completely covered by an insulating material that inhibits electrical pulse emission.

11. The electrical lead of claim 1, wherein the plurality of raised sections each has a radial span of 30-90 degrees.

12. The electrical lead of claim 1, wherein the face of the at least one of the raised sections is circular.

13. An electrical lead comprising:
a cylindrical lead body including an outer surface, a proximal end, a distal end, and a longitudinal axis extending therethrough;
at least one row of directional electrodes disposed along the longitudinal axis of the lead body; and
at least one unitary electrode;
wherein:
at least one of the directional electrodes includes at least one of (a) a raised section and a recessed section that is integral with and extends from the raised section and anchors the respective directional electrode to the cylindrical body, and (b) anchoring holes;
each of the at least one unitary electrode includes a respective plurality of raised and exposed sections connected to each other by at least one respective recessed non-exposed section;
the number of directional electrodes of each respective one of the at least one row of directional electrodes is equal to the number of raised sections of each of the at least one unitary electrode; and
the raised sections of the at least one unitary electrode are radially aligned with the directional electrodes.

14. The electrical lead of claim 13, wherein:
the at least one unitary electrode includes two unitary electrodes; and
the at least one row of directional electrodes comprises two rows of directional electrodes located between the two unitary electrodes.

15. An electrical lead comprising:
a cylindrical lead body including an outer surface, a proximal end, a distal end, and a longitudinal axis extending therethrough; and
at least one row of directional electrodes disposed along the longitudinal axis of the lead body;
wherein:
at least one of the directional electrodes includes at least one of (a) a raised section and a recessed section that is integral with and extends from the raised section and anchors the respective directional electrode to the cylindrical body, and (b) anchoring holes;
the at least one row of directional electrodes includes a row that includes a plurality of directional electrodes that are at a same longitudinal position of the cylindrical lead body and are radially offset from each other;
a first one of the plurality of directional electrodes includes, at a first side thereof:
a first recessed section extending at a top of the respective electrode towards a first side of a second of the plurality of directional electrodes which is adjacent to the first side of the first directional electrode; and
a second recessed section extending at a bottom of the respective electrode towards the first side of the second directional electrode;
the second directional electrode includes a recessed section at the first side thereof and which extends towards the first side of the first directional electrode; and
at least one of:
(a) the recessed section of the second directional electrode is axially positioned between the axial positions of the first and second recessed sections of the first side of the first directional electrode, and no recessed section extends from the first side of the second directional electrode in a direction towards the first side of the first directional electrode at the same axial positions as those of the first and second recessed sections of the first directional electrode; and
(b) the recessed section of the second directional electrode is surrounded by the first and second recessed sections of the first side of the first directional electrode.

16. The electrical lead of claim 15, wherein the recessed section of the second directional electrode is surrounded by the first and second recessed sections of the first side of the first directional electrode.

17. The electrical lead of claim 15, wherein the recessed section of the second directional electrode is axially positioned between the axial positions of the first and second recessed sections of the first side of the first directional electrode, and no recessed section extends from the first side of the second directional electrode in the direction towards the first side of the first directional electrode at the same axial positions as those of the first and second recessed sections of the first directional electrode.

18. An electrical lead comprising:
a cylindrical lead body including an outer surface, a proximal end, a distal end, and a longitudinal axis extending therethrough;
a unitary electrode that is disposed along the longitudinal axis of the body, wherein an outer surface of the unitary electrode is stepped forming a plurality of raised sections and at least one recessed section, and an inner surface of the unitary electrode, opposite the outer surface, is smooth;
an insulating material covering the at least one recessed section, wherein the plurality of raised sections are exposed surfaces of the electrical lead which are electrically connected to each other via the at least one recessed section; and
a row of directional electrodes at a single longitudinal position of the electrical lead and which are electrically isolated from each other;
wherein:
the electrical lead is configured to output electrical pulses via the exposed surfaces and via the directional electrodes;
electrical output is inhibited at the at east one recessed section by the insulating material; and
the exposed surfaces are at the same radial positions of the electrical lead as are the directional electrodes.

19. An electrical lead comprising:
a cylindrical lead body including an outer surface, a proximal end, a distal end and a longitudinal axis extending therethrough;
a unitary electrode that is disposed along the longitudinal axis of the body, wherein an outer surface of the unitary electrode is stepped forming a plurality of raised sections and at least one recessed section, and an inner surface of the unitary electrode, opposite the outer surface, is smooth;
an insulating material covering the at least one recessed section, wherein the plurality of raised sections are exposed surfaces of the electrical lead which are electrically connected to each other via the at least one recessed section; and
a row of directional electrodes at a single longitudinal position of the electrical lead and which are electrically isolated from each other;
wherein:
the electrical lead is configured to output electrical pulses via the exposed surfaces and via the directional electrodes;
electrical output is inhibited at the at least one recessed section by the insulating material; and
the exposed surfaces are radially misaligned with the directional electrodes, such that current of the electrical lead flows longitudinally with a bias in a radial direction.

* * * * *